United States Patent
Fonteyne et al.

(10) Patent No.: US 8,056,716 B2
(45) Date of Patent: Nov. 15, 2011

(54) TAMPER-EVIDENT PUSH-THROUGH PACKAGING

(75) Inventors: Gerard Fonteyne, Evergem (BE); Tony Malfait, Rollegem-Kapelle (BE); Erik Bögels, Lanaken (BE); Kris Buysens, Oudenaarde (BE)

(73) Assignee: Amcor Flexibles Transpac NV, Zaventem (BE)

( * ) Notice: Subject to any disclaimer, the term of this patent is extended or adjusted under 35 U.S.C. 154(b) by 0 days.

(21) Appl. No.: 12/864,757

(22) PCT Filed: Jan. 28, 2009

(86) PCT No.: PCT/EP2009/050942
§ 371 (c)(1),
(2), (4) Date: Jul. 27, 2010

(87) PCT Pub. No.: WO2009/095407
PCT Pub. Date: Aug. 6, 2009

(65) Prior Publication Data
US 2010/0314278 A1    Dec. 16, 2010

(30) Foreign Application Priority Data

Jan. 30, 2008 (EP) .................................. 08447002

(51) Int. Cl.
| | |
|---|---|
| *B65D 83/10* | (2006.01) |
| *B65D 41/00* | (2006.01) |
| *B32B 1/08* | (2006.01) |
| *B32B 27/08* | (2006.01) |

(52) U.S. Cl. ..................... 206/365; 206/807; 220/359.3; 428/35.7

(58) Field of Classification Search .......... 206/363–365, 206/438, 528, 531, 532, 538, 539, 807; 220/359.3; 428/35.7
See application file for complete search history.

(56) References Cited

U.S. PATENT DOCUMENTS

| | | | |
|---|---|---|---|
| 4,169,531 A | 10/1979 | Wood | |
| 5,172,812 A | 12/1992 | Wharton et al. | |
| 5,522,506 A | 6/1996 | Roulin et al. | |
| 5,568,865 A * | 10/1996 | Mase et al. | 206/438 |
| 5,690,222 A * | 11/1997 | Peters | 206/364 |

(Continued)

FOREIGN PATENT DOCUMENTS

| | | |
|---|---|---|
| DE | 2543069 A1 | 3/1977 |
| DE | 19613959 A1 | 10/1997 |
| EP | 0959020 A1 | 11/1999 |

*Primary Examiner* — Bryon Gehman
(74) *Attorney, Agent, or Firm* — Reinhart Boerner Van Deuren P.C.

(57) ABSTRACT

The present invention relates to a tamper-evident push-through packaging secured against fraudulent reuse comprising: —a polymer base web (1) comprising at least one pocket; —a multilayer lidding film (2) covering said pocket, said multilayer lidding film (2) comprising on its seal side a coextruded polymer film, said coextruded polymer film comprising a push-through polymer layer (3) sealed on the base web by a permanent seal and a peelable protective polymer layer (4), the polymers of both layers (3,4) being incompatible and in direct contact with each other, without interlayer, the adhesion between said push-through polymer layer (3) and said peelable protective polymer layer (4) being lower than the seal strength between said polymer base web (1) and said push-through polymer layer (3), wherein, in use, the push-trough layer leaves a seal seam (6), after removing the part of the push-trough layer (3) covering the pocket and wherein said protective layer (4) cannot be resealed by a heat sealing process on said seal seam (6).

12 Claims, 4 Drawing Sheets

U.S. PATENT DOCUMENTS

| | | | |
|---|---|---|---|
| 5,758,774 A * | 6/1998 | Leblong | 206/531 |
| 5,785,180 A | 7/1998 | Dressel et al. | |
| 6,006,913 A | 12/1999 | Lüdemann et al. | |
| 7,354,635 B2 * | 4/2008 | Malfait et al. | 428/35.7 |
| 7,919,171 B2 * | 4/2011 | Young | 206/528 |
| 2005/0003155 A1 | 1/2005 | Huffer | |
| 2005/0139505 A1 * | 6/2005 | Miller et al. | 206/528 |

\* cited by examiner

TAMPER-EVIDENT PUSH-THROUGH PACKAGING

CROSS-REFERENCE TO RELATED APPLICATIONS

This patent application is the National Stage of International Application No. PCT/EP2009/050942, filed Jan. 28, 2009, that claims the benefit of European Application No. 08447002.0, filed Jan. 30, 2008, the entire teachings and disclosure of which are incorporated herein by reference thereto.

FIELD OF THE INVENTION

The present invention relates to a packaging, in particular a thermoformed packaging for medical devices with a multilayer lidding film, said lidding film comprising a coextruded combination of a protective peelable polymer layer and a push-through polymer layer; both polymer layers being incompatible and in direct contact, without any adhesion layer, and the packaging being secured against fraudulent reuse, since it is impossible to reseal the layers by heat due to the incompatibility of their polymers.

STATE OF THE ART

Various packaging's for medical devices comprise a heat-sealable, peelable lidding film that can be heat-sealed again after it has been opened. While these types of packages are preferred because of their ease of opening, the risk of fraudulent reuse has now become a problem. In the case of pre-filled syringes for example, refilling and repacking by malicious individuals constitutes a major public health hazard.

The present invention describes a packaging material that prevents heat-resealing after use and that is nevertheless easy to open, as no cutting tools are required. Besides the major security feature of being non-reclosable by heat-seal, other features providing tamper evidence such as differences in colours or aspects between the push-through layer and the peelable protective layer may be foreseen.

Document U.S. Pat. No. 5,522,506 discloses a push-through container comprising a lidding film made of a polyolefin or polyester-based layer with a filler to adjust its mechanical properties. The filler is added in order to reduce the elasticity of the push-through film. Thus, the content can be easily pushed through the film.

Document EP 0 959 020 discloses a manipulation-proof packaging having a lidding film comprising a push-through plastic layer, a peelable adhesive layer joining a third, resistant push-through top layer, the particular composition of said push-through layer being described in U.S. Pat. No. 5,522,506.

Document DE 19613959 discloses a packaging wherein the lidding film comprises a pull-off protective layer, said pull-off layer being peelably connected to a push-through layer by means of an adhesive peelable layer, and said push-through layer being connected to the base web by means of a sealant layer.

Document U.S. Pat. No. 5,172,812 discloses a lidding closure comprising a push-through layer laminated by means of a peelable adhesive on a paperboard sheet.

The presence of an adhesive layer between the protective and push-through layers in DE 19613959, EP 0 959 020 and U.S. Pat. No. 5,172,812 renders it resealable by a standard heat-seal process. Furthermore, in order to achieve peelability between two layers, an additional layer having the desired peel strength level is usually added. Document U.S. Pat. No. 6,006,913 describes the composition of such a peelable layer. Another possibility is the use of a peelable adhesive.

Document US 2005/0003155 discloses a coextruded structure for making tamper-evident packaging wherein the Z tear strength of the inner layer is lower than the adhesive strength of the pressure-sensitive adhesive used to seal the package so that this inner layer is partly broken by the opening of the package and partly delaminates from the outer layer of the coextruded structure. Again, if this package cannot be resealed by simple pressure, it can be resealed by a heat-seal process and it is therefore not secured against fraudulent reuse.

SHORT DESCRIPTION OF THE DRAWINGS

FIG. 1 represents a cross-section view of the packaging of the present invention with the preliminary step of removing the protective polymer layer 4 by peeling by means of an opening aid 5, the push-through layer 3 remaining on the thermoformed base web 1.

FIG. 2 represents a cross-section view of the packaging of the present invention after peeling the protective layer 4 and the removal of the push-trough layer fragments. Layers 3 and 4 are essentially made of incompatible polymers and cannot be heat-sealed again on the remaining push-through layer residues 6.

FIG. 3 represents a cross-section view of the coextruded structure comprising a protective polymer layer 4 and a push-through polymer layer 3, the polymers of both layers 3 and 4 being incompatible.

Figure 6:
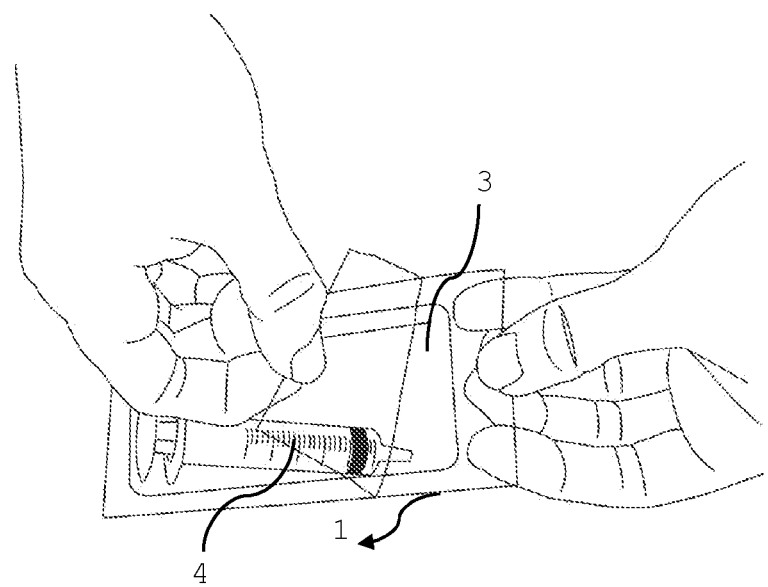
Figure 7:
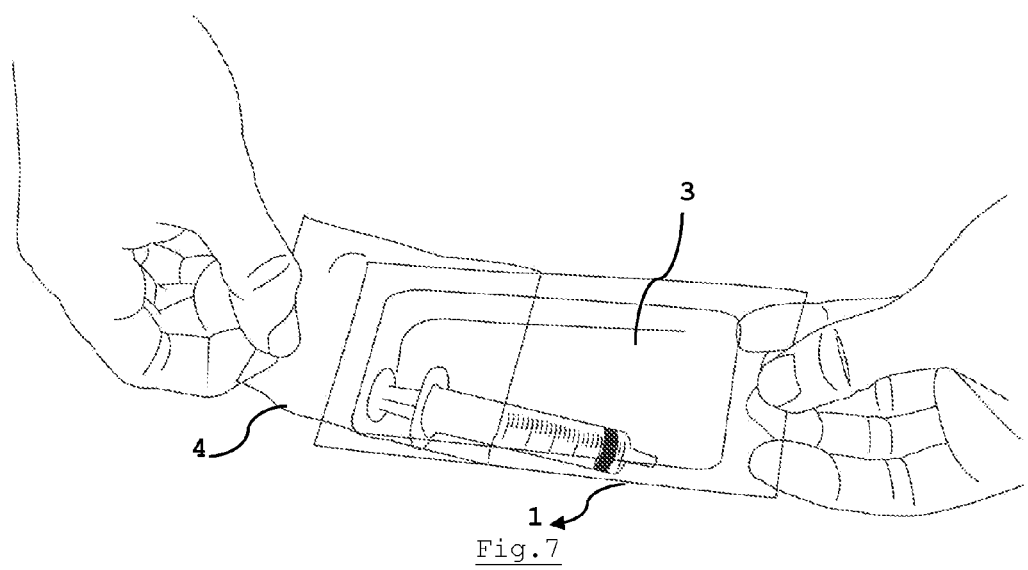

FIGS. 6 and 7 represent the procedure for peeling off the transparent protective polymer layer 4, the push-through polymer layer 3 also being transparent and not visible on the figure.

Figure 8:
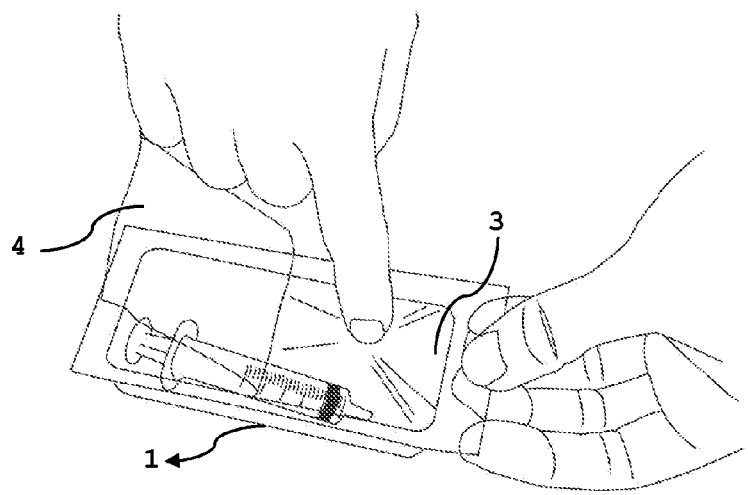

FIG. 8 represents the package after partial peeling of the protective polymer layer 4 with a finger pushing on the push-through polymer layer 3.

Figure 9:
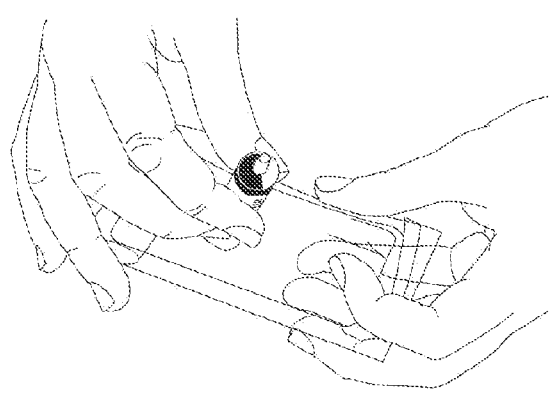

FIG. 9 represents the removal of the syringe from the package of the present invention.

Figure 10:
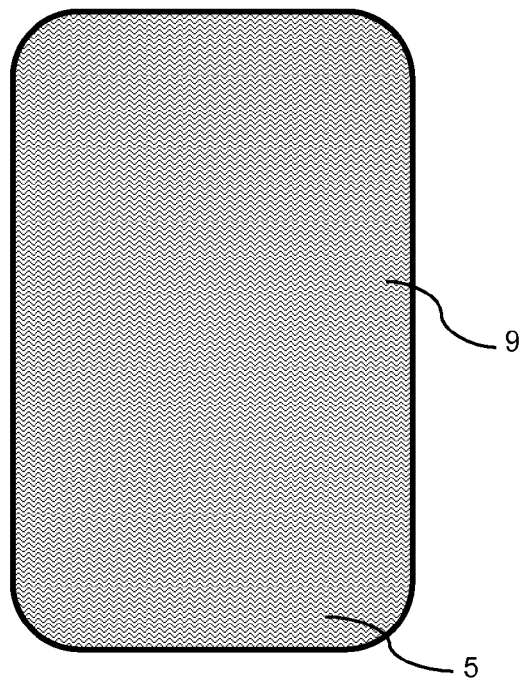

FIG. 10 represents a package with a push-through polymer layer 3 having a colour/aspect that is different from the protective polymer layer 4 before opening.

Figure 11:
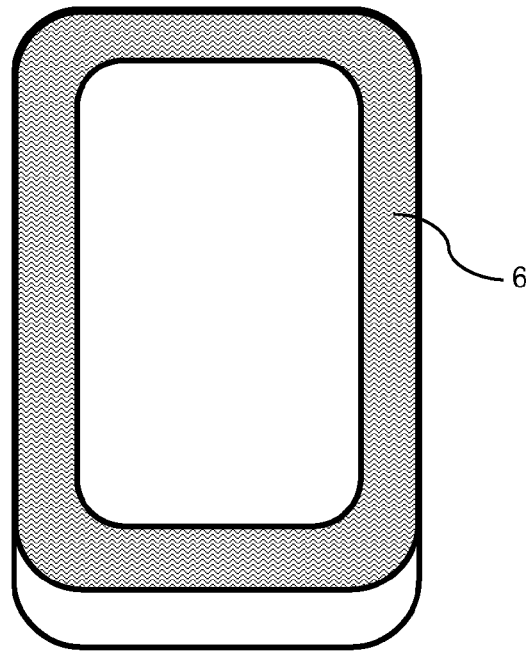

FIG. 11 represents a package with a push-through polymer layer 3 having a colour/aspect that is different from the protective polymer layer 4 after the pushed-through layer has been opened and removed, the push-through layer fragments 6 remaining on the base web 1 (seal seams).

AIMS OF THE INVENTION

The present invention aims to provide a tamper-evident push-through packaging secured against fraudulent heat reseal by conventional means in a heat-sealing process.

SUMMARY OF THE INVENTION

The present invention discloses evident push-through packaging secured against reuse comprising:
a polymer base web comprising at least one pocket;
a multilayer lidding film covering said pocket, said multilayer lidding film comprising on its seal side a 30 coextruded polymer film, said coextruded polymer film comprising a push-through polymer layer sealed on the base web by a permanent seal and a peelable protective polymer layer, the polymers of both layers being incompatible and in direct contact with each other, without interlayer, the adhesion between said push-through polymer layer and said peelable protective polymer layer being lower than the seal strength between said polymer base web and said push-through polymer layer, wherein, in use, the push-through layer leaves a seal seam, after removing the part of the push-through layer covering the pocket and wherein said protective layer cannot be resealed by a heat sealing process on said seal seam.

Particular preferred embodiments of the present invention comprise at least one or any suitable combination of the following features:

the multilayer lidding film comprises at least one additional layer;

the at least one additional layer is selected from the group consisting of paper, metal and polymer;

the adhesion between said push-through layer and said protective layer is between O.3N/15 mm and 3.5N/15 mm measured according to ASTM F88-00;

the puncture resistance of the push-through layer is between O.6N and 7N measured according to ASTM F1306-90;

the puncture resistance of the push-through layer is between 1.4N and 4N, measured according to ASTM F1306-90;

the thickness of the push-through layer is lower than 20 μm;

the thickness of the push-through layer is lower than 15 μm;

the combinations of the incompatible polymers of the push-through polymer layer and the peelable protective polymer layer are selected from the group consisting of PETG/PP block copolymer, PETG/LDPE, ethylene-propylene block copolymer/PETG, MDPE/PP, DPE/PETG and EMA/PA;

the push-through polymer layer comprises inorganic filler;

the push-through polymer layer has another colour and/or aspect than the protective polymer layer;

DETAILED DESCRIPTION OF THE INVENTION

The present invention takes advantage of the low adhesion between coextruded incompatible polymer layers.

The packaging of the present invention comprises a plastic base web 1, preferably thermoformed, and a multilayer lidding film 2. Said lidding film 2 comprises at least one coextruded structure with at least two layers of incompatible polymers coextruded without any adhesive inter layer. The absence of this adhesive interlayer renders the adhesion sufficient after coextrusion to maintain the integrity of the film during the shelf life of the product, but renders said adhesion too low to allow a reseal after peeling.

The push-through layer 3 of the lidding film is compatible with the base web and has to be chosen essentially among the same polymer family, so that it can be sealed by heat seal on said base web 1, forming a closed pocket containing for instance a medical device, said push-through layer 3 having a thickness and composition which can be easily pushed through to have access to said medical device.

In order to ease the opening of the package, a part of the lidding film 2 can remain unsealed, producing an opening aid 5, so that the user can grip said opening aid with his fingers and peel off the protective polymer layer 4.

The protective polymer layer 4 can be easily peeled-off from said push-through polymer layer 3. The peel strength between the layer 3 and 4 is such that an easy peeling is possible without tearing the push-through polymer layer 4.

This protective polymer layer 4 provides, along with possible additional coextruded or laminated layers, both the necessary mechanical strength to fulfil his protective function and, if needed, a barrier against oxygen/water.

The required peel strength between the push-through polymer layer 3 and the protective layer 4 is achieved by using coextrusion techniques. The coextrusion of a polymer layer A and a polymer layer B, with A and B being specific incompatible polymer types, provides the desired peel strength.

The definition of incompatible polymers, although being frequently used by the man skilled in the art, is not univocal in the technical community, some authors defining it as immiscible polymers, others by interfacial tension or interfacial adhesion levels. In the following paragraphs of the present document is defined what should be understood by incompatible polymers.

Two polymers are said to be non-miscible when the free energy of the mixture ($\Delta G_{mix}$) is greater than or equal to zero.

Two polymers are said to be non-miscible and compatible when the free energy of the mixture is greater than or equal to zero, when modifications of the respective vitreous transition temperatures (Tg) of the partners can be observed, when the mixture has a Flory-Huggins parameter $\chi$ (chi) that is low but greater than zero, and when the interface tension is low. The interface tension, which is proportional to the square of the Flory-Huggins parameter $\chi$ (chi), is considered "low" when it is between 0 and 2 mN/m.

Two polymers are said to be non-miscible and incompatible when the free energy of the mixture is greater than or equal to zero, when no modification of the respective vitreous transition temperatures (Tg) of the partners can be observed, when the mixture has a Flory-Huggins parameter $\chi$ (chi) greater than zero, and when the interface tension is high. The interface tension, which is proportional to the square of the Flory-Huggins parameter $\chi$ (chi), is considered "high" when it is greater than 2 mN/m.

The push-through and protective layers 3 and 4, which are non-miscible and incompatible, adhere sufficiently to each other in their "co-extruded layer state" but do not provide sufficient seal strength once they are peeled off and submitted to a heat-seal trial.

Figure 1:
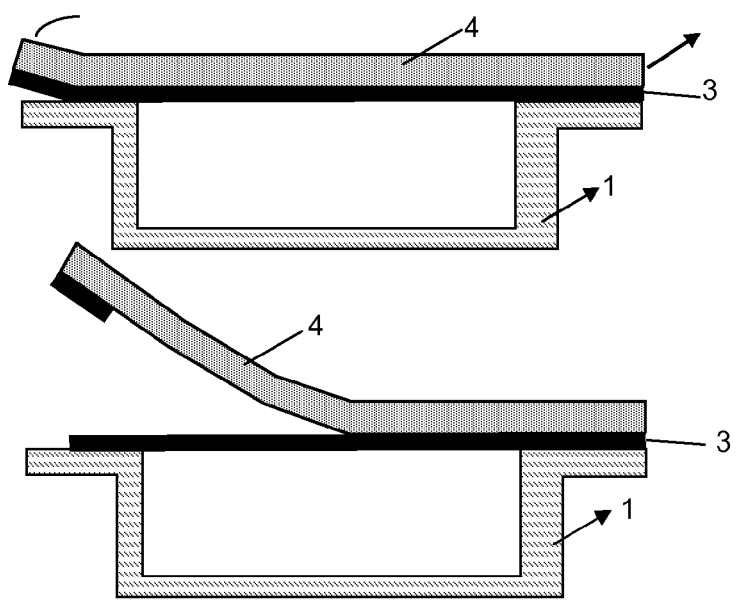
Figure 2:
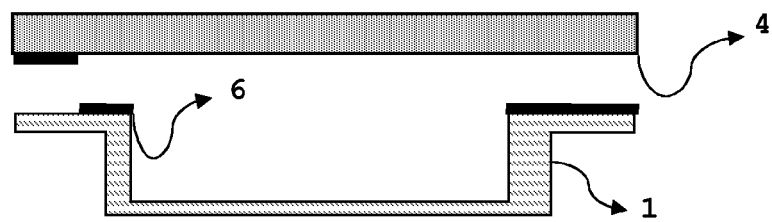

When opening the package by using the lidding film opening aid 5, said push-through polymer layer 3 breaks at the seal and the protective polymer layer 4 starts peeling (see FIG. 1). Once the protective polymer layer 4 has been peeled off, the push-through polymer layer 3, which is still intact and covering the packed item, is pushed through in order to have access to the packed item.

Thanks to the use of coextrusion techniques, the additional application of a peelable adhesive layer can be avoided. According to this coextrusion technique, it is also possible to produce a very thin push-through polymer layer 3. A thickness below 20 μm, preferably 15 μm or even 10 μm is easily achievable, and this low thickness is favourable for the ease of push-through. The lamination of such film thickness is, in practice, extremely difficult.

The nature and thickness of this thin push-through polymer layer 3 is preferably such that:

it provides the desired peel-strength with the co-extruded protective polymer layer 4 (incompatibility);

it can be very easily ruptured;

it is heat-sealable (firm seal) onto the base web 1, not requiring an additional heat-seal lacquer.

EXAMPLES

The following examples are only illustrative for the packaging of the present invention.

The base web 1 is a common plastic web comprising one or more layer based for instance on PETG, PET-GAG, APET, PVC, PP, Nylon//PE, PP/PE, PETG//PE, APET/PE, . . . This type of base webs is widely used for packed medical devices, syringes and the like.

Figure 3:
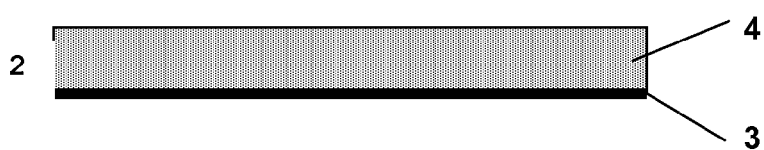
Figure 4:
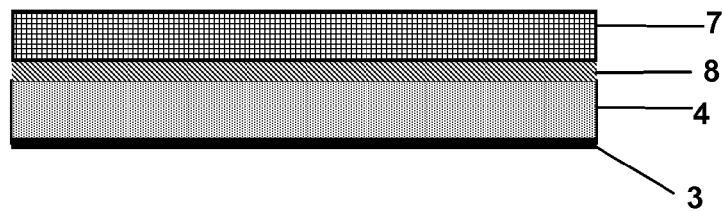
FIG. 4 represents a cross section view of a multilayer lidding film comprising additional coextruded or laminated layers 8,7.
Figure 5:
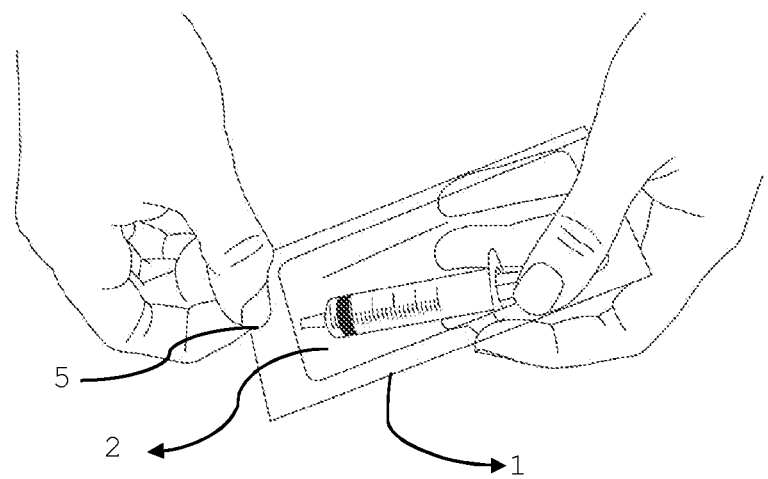
FIG. 5 represents the closed package of the present invention with a syringe inside.

The multilayer lidding film 2 comprises a peelable co-extruded film with at least a push-through polymer layer 3 on one side and a protective polymer layer on the other side. The coextruded film of two layers (3,4) can be used alone (FIG. 3) or in combination with further additional layers (FIG. 4).

The desired peel strength between the push-through polymer layer 3 and the protective layer 4 can be achieved by co-extruding specific types of polymers. Examples of incompatible polymer combinations that result in the desired interlayer adhesion are PETG/PP, PE/APET, APET/PE, PETG/PE, PE/PETG, PE/PA, PE/PP, PP/PE, EMA/PA. It is important to emphasize here that those structures are produced without tie layers between the layers 3 and 4. They are interlayer-free.

The 180°-peel strength between the push-through polymer layer 3 and the protective polymer layer 4 varies between 0.3-3.5N/15 mm.

The puncture resistance of the push-through layer, as measured according to ASTM F1306-90, should be lower than $7N/8 \text{ mm}^2$, preferably lower than $4N/8 \text{ mm}^2$ and this at a film thickness of maximum 25 μm, and preferably of maximum 20 μm.

Depending on the nature and the thickness of the push-through polymer layer 3, a certain amount of filler may be added in order to give said layer the desired rupture properties, such as disclosed in U.S. Pat. No. 5,522,506. The addition of such filler is not needed when the thickness of the push-through polymer layer 3 is sufficiently low. The absence of filler allows to maintain the transparency of the layer, if needed.

The polymers used in both layer 3 and 4 may be random, block, alternating, and/or graft copolymers of the above-mentioned types of polymers prepared by polymerising two or more comonomers and thus including dipolymers, terpolymers, such as copolymers of polyethylene and vinylacetate (EVA), methyl acrylate (EMA), (meth) acrylic acid, . . . .

The above-mentioned polymers may be blended with one or more other types of polymer providing the required mechanical/sealing properties and the required adhesion and peelability between the layers 3 and 4 is given.

In case the coextruded protective polymer layer 4 has a low softening temperature (Tm or Tg), such as LDPE or PETG, the coextrusion or lamination of an additional layer with a polymer having a higher softening temperature is recommended in order to be able to seal the multilayer lidding film 2 onto the base web 1.

The push-through polymer layer 3 is preferably made of a thin layer of less than 20 μm that can be both easily ruptured and heat-sealed (tight seal) onto the base web 1.

In order to optimize the properties (puncture resistance, tear resistance, thermal resistance, barrier properties, . . . ) of the multilayer lidding film 2, laminating the coextruded film (3,4) with at least one additional layer may be required. In this case, the structure of the multilayer lidding film 2 is the following (FIG. 4):
- 3: a push-through co-extruded polymer layer that can easily be ruptured (thin layer)
- 4: a protective co-extruded polymer layer, peelable from push-through layer 3
- 7: a laminated or coextruded additional layer
- 8: an adhesive layer (tie layer/interlayer)

Additional layers that are of interest for lamination with the co-extruded film (3,4) are OPET, OPA, PA, OPP, aluminium foil containing a film, paper containing film, . . . (FIG. 4).

In order to improve the barrier properties of the lidding film, a vapour-deposited layer of aluminium, aluminiumoxide, siliciumoxide, . . . may be applied on this protective film layer (OPET, OPP are widely used for this purpose). The lamination with an aluminium foil type of film may also be of interest in this perspective. The laminated protective film structure 7 may be a laminate itself of two or more layers as well. Both adhesive lamination and extrusion lamination may be used.

The main security feature provided by the claimed packaging is the impossibility to reseal the lidding film 2 by conventional sealing methods. This is due to always remaining residual material 6 of the push-through layer that is left on the seal seam of the bottom web 1. Once the package has been opened and the ruptured push-through polymer layer 3 covering the pocket has been removed, a subsequent heat reseal becomes impossible. This unique feature can only be achieved by combining specific polymer types in the push-through polymer layer 3 and the protective polymer layer 4, as explained above.

Another possible security feature providing tamper evidence is the use of a push-through polymer layer 3 having another colour/aspect than the protective polymer layer 4. Once the package has been opened and the push-through polymer layer 3 has been ruptured and removed, it is impossible to reproduce the aspect of the original package, as illustrated in FIGS. 10 and 11.

Example 1

A packaging comprising
- a thermoformed plastic base web 1 of PETG, 300 μm
- a multilayer lidding film 2 comprising a coextruded film obtained by the coextrusion of
- a push-through layer 3 of PETG (Eaststar 6763 from Eastman-Kodak), 8 μm and
- a peelable protective layer 4 of PP block-copolymer (RB307MO from Borealis), 30 μm The coextrudate (3,4) is then laminated on the PP side with an additional layer 7 of OPET (Mylar 800 DuPont Teijin Films), 12 μm, using a 2K-PU adhesive 8.

Example 2

A packaging comprising
- a thermoformed plastic base web 1 of PP, 300 μm
- a multilayer lidding film 2 comprising a coextruded film obtained by the coextrusion of:
- a push-through layer 3 of ethylen-propylene block-copolymer (RD735CF from Borealis), 5 μm
- a peelable protective layer 4 of PETG (Eaststar 6763 from Eastman-Kodak), 35 μm The coextrudate (3,4) is then laminated on the PETG side with an additional layer 7 of OPA (Capran 1200 from Honeywell), 15 μm, using a 2K-PU adhesive 8.

Example 3

A packaging comprising
a thermoformed plastic base web 1 of APET/PE, 240 μm
a multilayer lidding film 2 comprising a coextruded film obtained by the coextrusion of:
a push-through layer 3 of MDPE (LD 151BW from ExxonMobil), 10 μm
a peelable protective layer 4 of a PP block-copolymer (BB213CF from Borealis), 40 μm
The coextrudate (3,4) is then laminated on the PP side with an additional layer 7 of OPET (Mylar 800 from DuPont Teijin Films), 12 μm using a 2K-PU adhesive 8.

Example 4

A packaging comprising
a thermoformed plastic base web 1 of PVC, 240 μm
a multilayer lidding film 2 comprising a coextruded film obtained by the coextrusion of:
a push-through layer 3 of a copolymer of ethylene and methylacrylate (Elvaloy 1218AC from Dupont) containing 30% calcium carbonate, 10 μm
a peelable protective layer 4 of PA (Akulon F132-F from DSM), 40 μm
This lidding film is not further laminated, since the polyamide layer already has a high melting temperature.

Example 5

Packaging comprising
a thermoformed plastic base web 1 of PETG, 240 μm
a multilayer lidding film 2 comprising a coextruded film obtained by the coextrusion of:
a push-through layer 3 of PETG (Eaststar 6763 from Eastman), 15 μm
a peelable protective layer 4 of LDPE (Sabic 2201 TH00 from Sabic), 50 μm
The coextrudate (3,4) is then laminated on the LDPE side with an additional layer 7 of AlOx coated oriented PET (Camclear RHB-Y from AMCOR-Camvac), 12 μm, using a 2K-PU adhesive 8.

Example 6

A packaging comprising
a thermoformed plastic base web 1 of PETG/PE, 300 μm
a multilayer lidding film 2 comprising a coextruded film obtained by the coextrusion of:
a push-through layer 3 of 99% MDPE (LD 151BW from ExxonMobil)+1% masterbatch red pigment (Polybatch 5020 from Schulman), 20 μm
a peelable protective layer 4 of PETG (Eaststar 6763 from Eastman), 30 μm
The coextrudate (3,4) is then laminated on the PETG side with an additional layer 7 of a laminate of Aluminium foil (from Hydro Aluminium) 12 μm and oriented PET (Mylar 800 DuPont Teijin Films) 12 μm using a 2K-PU adhesive 8.
Preparation of the Packaging, Test Methods and Test Results
The base web 1 is thermoformed on a Multivac packaging machine (packs of 6×13 cm, 1.5 cm deep) and the multilayer lidding film is sealed on the base web using the following conditions:
Pressure: 0.2-0.6 MPa
Temperature: 140-180° C.
Sealing time: 2-8 seconds Properties of the Coextrudate (3,4) of the Push-Through Polymer Layer 3 and the Peelable Protective Polymer Layer 4
Peel strength measurements were performed according to ASTM F88-00 with the following parameters:
Rate of grip separation: 300 mm/min
Tail holding method: supported 180°
Sample width: 15 mm
Puncture resistance measurements were performed according to the standard ASTM F1306-90, with the following parameters:
3.2 mm diameter hemispherical (biaxial stress) probe (8 mm2)
Cross head speed: 25 mm/min

| Features | Ex 1 | Ex 2 | Ex 3 | Ex 4 | Ex 5 | Ex 6 |
|---|---|---|---|---|---|---|
| Peel strength between layers 3 and 4 (N/15 mm); supported 180° | 0.3 | 0.3 | 0.6 | 3.5 | 0.9 | 0.75 |
| Puncture resistance (N/8 mm$^2$) of the push through polymer layer 3 | 4 | 1.4 | 1.9 | 0.6 | 7 | 3.5 |

FIGURE KEYS

1. Polymer base web
2. Multilayer lidding film
3. Push-through polymer layer
4. Protective polymer layer
5. Opening aid
6. Push-through layer residue on the base web after peeling and opening (residual seal seam)
7. Additional protective layer, laminated or coextruded onto the protective polymer layer (4)
8. Adhesive layer
9. Sealed surfaces

The invention claimed is:
1. Tamper-evident push-through packaging secured against fraudulent reuse comprising: —a polymer base web (1) comprising at least one pocket;
a multilayer lidding film (2) covering said at least one pocket, said multilayer lidding film (2) comprising on a seal side thereof a coextruded polymer film, said coextruded polymer film comprising a push-through polymer layer (3) sealed on the base web by a permanent seal and a peelable protective polymer layer (4), the polymers of both layers (3,4) being incompatible and in direct contact with each other, without an interlayer, the adhesion between said push-through polymer layer (3) and said peelable protective polymer layer (4) being lower than the seal strength between said polymer base web (1) and said push-through polymer layer (3), wherein, in use, the push-through layer leaves a seal seam (6), after removing the part of the push-through layer (3) covering the at least one pocket and wherein said protective layer (4) cannot be resealed by a heat sealing process on said seal seam (6).
2. A tamper-evident push-through packaging according to claim 1, wherein said multilayer lidding film (2) comprises at least one additional layer.
3. A tamper-evident push-through packaging according to claim 2, wherein said at least one additional layer is selected from the group consisting of paper, metal and polymer.

4. A tamper-evident push-through packaging according to claim 1, wherein the adhesion between said push-through layer (3) and said protective layer (4) is between 0.3N/15 mm and 3.5N/15 mm measured according to ASTM F88-00.

5. A tamper-evident push-through packaging according to claim 1, wherein the puncture resistance of the push-through layer (3) is between 0.6 N and 7 N, measured according to ASTM F1306-90.

6. A tamper-evident push-through packaging according to claim 1, wherein the puncture resistance of the push-through layer (3) is between 1.4 N and 4 N, measured according to ASTM F1306-90.

7. A tamper-evident push-through packaging according to claim 1, wherein the thickness of the push-through layer (3) is lower than 20 μm.

8. A tamper-evident push-through packaging according to claim 1, wherein the thickness of the push-through layer (3) is lower than 15 μm.

9. A tamper-evident push-through packaging according to claim 1, wherein the combinations of the incompatible polymers of the push-through polymer layer (3) and the peelable protective polymer layer (4) are selected from the group consisting of PETG and PP block copolymer; PETG and LDPE; ethylene-propylene block copolymer and PETG; MDPE and PP; MDPE and PETG; and EMA and PA.

10. A tamper-evident push-through packaging according to claim 1, wherein the push-through polymer layer (3) comprises inorganic filler.

11. A tamper-evident push-through packaging according to claim 1, wherein the push-through polymer layer (3) has another colour or aspect than the protective polymer layer (4); or another colour and aspect than the protective polymer layer (4).

12. A tamper-evident push-through packaging according to claim 1, wherein the compatibility between the polymers of the push-through layer (3) and the base web (1) ensures the presence of a permanent seam (6) permanently sealed onto the base web (1) even after removing the part of the push-through layer covering the at least one pocket.

* * * * *

UNITED STATES PATENT AND TRADEMARK OFFICE
CERTIFICATE OF CORRECTION

PATENT NO.        : 8,056,716 B2
APPLICATION NO.   : 12/864757
DATED             : November 15, 2011
INVENTOR(S)       : Gerard Fonteyne et al.

Page 1 of 1

It is certified that error appears in the above-identified patent and that said Letters Patent is hereby corrected as shown below:

Title Page: Item 57
Replace the Abstract with:

The present invention relates to a tamper-evident push-through packaging secured against fraudulent reuse comprising: - a polymer base web (1) comprising at least one pocket; - a multilayer lidding film (2) covering the pocket, the multilayer lidding film (2) comprising on its seal side a coextruded polymer film, the coextruded polymer film comprising a push-through polymer layer (3) sealed on the base web by a permanent seal and a peelable protective polymer layer (4), the polymers of both layers (3,4) being incompatible and in direct contact with each other, without interlayer, the adhesion between the push-through polymer layer (3) and the peelable protective polymer layer (4) being lower than the seal strength between the polymer base web (1) and the push-through polymer layer (3), wherein, in use, the push-through layer leaves a seal seam (6), after removing the part of the push-through layer (3) covering the pocket and wherein the protective layer (4) cannot be resealed by a heat sealing process on the seal seam (6).

Signed and Sealed this
Twenty-fourth Day of January, 2012

David J. Kappos
*Director of the United States Patent and Trademark Office*